United States Patent [19]
Seiler et al.

[11] 4,196,139
[45] Apr. 1, 1980

[54] PROCESS FOR THE PRODUCTION OF ETHYLSILANES

[75] Inventors: Claus-Dietrich Seiler, Rheinfelden; Hans-Joachim Vahlensieck, Wehr, both of Fed. Rep. of Germany

[73] Assignee: Dynamit Nobel Aktiengesellschaft, Troisdorf, Fed. Rep. of Germany

[21] Appl. No.: 28,427

[22] Filed: Apr. 9, 1979

[30] Foreign Application Priority Data

Apr. 13, 1978 [DE] Fed. Rep. of Germany ....... 2815978

[51] Int. Cl.$^2$ ................................................ C07F 7/08
[52] U.S. Cl. ..................................... 556/479; 556/481
[58] Field of Search ................................. 260/448.2 E

[56] References Cited

U.S. PATENT DOCUMENTS

| | | | |
|---|---|---|---|
| 2,823,218 | 2/1958 | Speier | 260/448.2 E |
| 4,055,584 | 10/1977 | Kny | 260/448.2 E |

*Primary Examiner*—Paul F. Shaver
*Attorney, Agent, or Firm*—Sprung, Felfe, Horn, Lynch & Kramer

[57] ABSTRACT

A process for the production of an ethylsilane, which comprises contacting vinyl chloride with hydrogen silane in the presence of a platinum or palladium catalyst at a pressure of not less than 5 bars.

4 Claims, No Drawings

PROCESS FOR THE PRODUCTION OF ETHYLSILANES

The object of the present invention is a process for the production of ethylsilane in which hydrogen silane and vinyl chloride are used as starting products.

In the past, ethylchlorosilanes have been prepared by different methods. Ethyltrichlorosilane, for example, may be prepared by reacting ethylene with trichlorosilane in stoichiometric amounts, or also in non-stoichiometric amounts in favor of one compound or the other, continuously or discontinuously, under pressure and at elevated temperature. With this operating procedure, more or less large amounts of by-products such as butyl-, hexyl- and octyltrichlorosilane always form in addition to the main component, ethyltrichlorosilane. The formation of these by-products is due to the di-and trimerization of the ethylene which takes place under the reaction conditions. Moreover, with this operating procedure it is difficult to obtain 100% conversion of the ethylene even when it is used in stoichiometric deficiency.

It is further known to prepare ethylsilanes by catalytic reaction of ethylene with hydrogen silanes in the presence of platinum or rhodium catalysts. In this reaction, known as an addition reaction, ethylene, in the case of preparation of ethyltrichlorisolanes, for example, is passed through trichlorosilane or mixtures of trichlorosilane and higher-boiling inert components such as hexachlorodisiloxane in the presence of hexachloroplatinic acid or platinum on activated charcoal. In this procedure the same byproduct problems arise as in the aforesaid pressure synthesis. Another drawback of this operating procedure is that not all of the ethylene is converted, so that provision must be incorporated in the apparatus for recycling the unreacted ethylene. Moreover, difficulties are experienced in reproducing the catalyst activity when it has dropped.

To overcome these drawbacks of the addition reaction, it has also been proposed to produce ethyltrichlorosilane by the following procedure: Trichlorosilane is kept boiling in a receiver, and the rising $SiHCl_3$ vapors are conducted to a condenser for condensation, the catalyst bed consisting of platinum on activated charcoal being bypassed. The condensate is recycled, along with ethylene introduced in parallel, into the boiling trichlorosilane mixture through the catalyst bed by way of an air lock or sluice. While the yields obtained by this procedure are as high as the lower portion of the 90% range, there is always the problem of distillative separation of telomerization products (butyltrichlorosilane and hexyltrichlorosilane).

Thus the problem has been to produce ethylsilanes in such a way that no higher alkylsilanes are formed and that the starting products used are converted as nearly quantitatively as possible.

This problem has now been solved by a process for the production of ethylsilanes which is characterized in that vinyl chloride is reacted with hydrogen silanes in the presence of a platinum or palladium catalyst at a pressure of not less than 5 bars.

In a preferred embodiment, the catalyst is not suspended in the reaction mixture but is disposed between the latter and a condenser. In the condenser, the vapors of the reaction mixture, which is kept boiling, are condensed, and the condensate then trickles through the catalyst back into the boiling reaction mixture. Suitable ways of carrying out this process are described in German Pat. No. 20 12 229.

A particularly advantageous mode of practicing this process consists in conducting the rising vapors to the condenser while bypassing the catalyst. The condensed vapors then trickle down, through suitable feeding means such as distributor plates, onto the catalyst and from there through appropriate air locks or sluices to the reaction mixture, which is kept boiling.

While in German Pat. No. 20 12 229 it is stated that in the process there described vinyl chloride, too, may be used as olefinic starting compound, the process there described relates to the addition reaction, which as such is known, and in which the olefinic component is added to the hydrogen silane without decomposition or cleavage of substituents. (See also German Pat. No. 10 69 148.) By analogy to the formation of ν-chloropropyltrichlorosilane from trichlorosilane and allyl chloride, it would have had to be expected here, too, that the reaction between trichlorosilane and vinyl chloride would result in a corresponding addition to the trichlorosilane, with formation of 1-chloroethyltrichlorosilane or 2-chloroethyltrichlorosilane, or both. Both compounds are known to be stable compounds and can be produced by another route. It is all the more surprising that with operation under pressure, and particularly with the preferred mode of operation, the vinyl chloride used is converted almost in its entirety to ethyltrichlorosilane.

Since in accordance with the invention, above-atmospheric pressure is employed, the latter is advantageously produced by appropriately raising the system temperature and closing the system. Care must be taken that the temperature at the point of condensation is not too much below the boiling point of the system at the predetermined pressure, as otherwise the desired system pressure will collapse.

In the preferred mode of operation, in which the catalyst is bypassed as the vapors of the reaction mixture are conducted to the condensing zone, provision must be incorporated in the apparatus for preventing the vapors from ascending through the catalyst. Such gas locks or sluices are known to the person skilled in the art. One such device suited for use is the siphon, for example; however, other gas shutoff valves may be used, disposed between receiver and catalyst.

The catalyst is advantageously disposed on a suitable carrier material, especially when it is disposed above the reaction mixture. A suitable carrier material is activated charcoal or $Al_2O_3$, for example. The catalysts may be used either in metallic form or as compounds (e.g., $H_2PtCl_6$). Pronounced activity is exhibited also by complex compounds of these metals, as described, for example, in German patent application No. DAS 12 71 712 or in German Pat. No. 19 37 904.

In general, both the hydrogen silanes and the vinyl chloride are first introduced into the receiver and then heated to ebullition. However, the hydrogen silane may also be introduced first and heated to ebullition under the desired pressure, the vinyl chloride then being metered in.

In accordance with the invention, the pressure should be at least 5 bars. For process-engineering reasons, the upper limit should be about 25 bars, although in principle the reaction in accordance with the invention may also be carried out at higher pressures. Thus, the preferred pressure is comprised between 8 and 25 bars. The pressure stated is "absolute."

The end of the reaction is signaled by the fact that the reaction mixture boils at constant temperature and also that the catalyst no longer heats up as condensate trickles through it.

The hydrogen silane used is preferably trichlorosilane. However, the reaction can also be carried out with alkylhydrogen halosilanes of the general formula H Si $R_p X_{3-p}$, where R is an alkyl radical having preferably from 1 to 4 carbon atoms, X is a halogen atom, preferably Br or Cl, or an alkoxy radical having from 1 to 4 carbon atoms, and p may assume values between 0 and 2. The hydrogen silane should preferably be present in excess. Preferably from 2 to 2.5 mols of hydrogen silane are used per mol of vinyl chloride.

Further examples of hydrogen silanes which may be used in accordance with the invention are dichlorosilane, methylhydrogen-dichlorosilane, dimethylhydrogen-chlorosilane, ethylhydrogen-dichlorosilane, trimethoxysilane, triethoxysilane and diethoxyhydrogensilane.

EXAMPLE 1 (comparative example)

Into a 10-liter steel autoclave, 20 mols (2.7 kg) of trichlorosilane is introduced. After the autoclave has been closed, 18 mols (504 g) of ethylene is injected from an ethylene-filled steel cylinder.

The autoclave so charged is heated to 325° C. over a period of 2 hours, maintained at that temperature for about 1.5 hours, and then cooled. The crude product is first analyzed by gas chromatography and then worked up distillatively. Apart from a residual ethylene content of about 2% (determined by measuring the area within the curve in the chromatogram), a ratio between the areas of ethyltrichlorosilane/butyltrichlorosilane/hexyltrichlorosilane of 85:12:3 was determined.

Working up of the crude product by distillation resulted in 1875 g of ethyltrichlorosilane, which represents a yield of 63.7%, based on the ethylene used.

EXAMPLE 2 (comparative example)

A 2-liter three-necked flask is inserted in a heating jacket. A low-temperature condenser is set onto one of the outer necks while into the other a gas feed pipe is set which extends all the way to the bottom of the flask and at its end discharges into a fritted plate for fine distribution of the gas. The middle neck is stoppered. 10 mols (1000 g) of trichlorosilane is introduced into the flask together with 1.5 g of chlorophatinic acid. After the low-temperature condenser has been connected to a brine supply of −38° C., the content of the flask is heated to ebullition. The introduction of ethylene through a precision-adjustment valve is then begun. After 37 hours, about 10 mols (280 g) of ethylene has been bubbled through the platinum-containing sump.

The reaction is discontinued at this point and an analysis by gas chromatography is performed on the reaction product. No residual ethylene content is determinable. The ratio of the areas of ethyltrichlorosilane/butyltrichlorosilane/hexyltrichlorosilane under the chromatogram curve is found to be 85:35:1.

Working up of the crude product by distillation yields 277 g of ethyltrichlorosilane and a sump product consisting essentially of butyltrichlorosilane (about 126 g).

Thus only about 32% of the ethylene charged has been converted, the rest having escaped in gaseous form.

The ethyltrichlorosilane yield is 17%, based on the ethylene charged to the reaction system.

EXAMPLE 3 (comparative example)

A steel apparatus constructed as follows is used:

A steel pipe is run from a steel still (capacity, about 10 liters; steam-heatable through an immersion heater) to the lower part of a tubular condenser (surface area, about 0.6 m$^2$). From the lower part of the condenser, a line runs downwardly to a steel pipe (diameter, 80 mm) in which 1000 ml of a platinum/activated charcoal catalyst is disposed. (Diameter, 2.3 mm; length, 5 m.) The platinum content is 1%, the bulk density, 0.45 g/cm$^3$.

From the bottom of the pipe containing the catalyst, a pipe bent to form a siphon (diameter, 12 mm) is run back into the cover of the still. The still itself is provided with a manometer and a temperature indicator. A temperature measuring point is also disposed in the center of the catalyst mass. The condenser is operated with water as coolant. The water supply is shut off as the experiment is started.

40 mols (5410 g) of trichlorosilane is introduced into the still. The system is brought to a pressure of from 10 to 12 bars by applying steam to the coils of the immersion heater. The associated still temperature is between 110° and 120° C. By carefully admitting water to the tubular condenser above the still, provision is made for condensation of the trichlorosilane vapors, and hence for trickling of the condensate through the activated-charcoal/catalyst bed. Over a period of 1 hour, 20 mols (560 g) of ethylene is introduced into the system.

The onset of the reaction is signaled by a temperature rise at the measuring point located in the catalyst bed. The end of the reaction is indicated by a corresponding temperature drop. After the temperature in the catalyst bed has been allowed to fall, the reaction product is discharged.

The gas-chromatographic analysis results in a ratio of the areas of ethyltrichlorosilane to butyltrichlorosilane of 92:4.

Distillative working up of the crude product produces 3008 g (18.4 mols) of ethyltrichlorosilane, which corresponds to a yield of about 92%, based on the ethylene used. 8% of the ethylene used has been consumed in the formation of butyltrichlorosilane.

EXAMPLE 4

Into the apparatus described in Example 3, 40 mols (5410 g) of trichlorosilane is introduced. The apparatus is operated in the manner there described. (Operating pressure, about 10 to 12 bars; operating temperature, about 110° to 120° C.) Over a period of one-half hour, 19.8 mols (1237 g) of vinyl chloride is fed into the system. Beginning and end of the reaction are indicated by a rise and corresponding drop in the catalyst-bed temperature.

After the temperature in the catalyst bed has been allowed to fall completely, the reaction product is discharged. Gas-chromatographic analysis shows that no vinyl chloride residue is detectable in the crude product. Apart from the ethyltrichlorosilane, no alkylsilane byproducts are detected.

Distillative working up of the crude product yields 3205 g (19.6 mols) of ethyltrichlorosilane. The yield therefore is 99%, based on the vinyl chloride used.

EXAMPLE 5

Into the apparatus described in Example 3, 40 mols (4600 g) of methylhydrogen dichlorosilane is introduced. The apparatus is operated as described in Example 3. (Operating pressure, 9 to 11 bars; operating temperature, 110° to 120° C.)

Over a period of one hour, 19.8 mols (1237 g) of vinyl chloride is fed into the system.

The start and end of the reaction are again indicated by a rise and corresponding drop in the catalyst-bed temperature.

After the temperature in the catalyst bed has fallen completely, the reaction product is discharged. Gas-chromatographic analysis again shows that no vinyl chloride residue is detectable in the crude product. Apart from ethylmethyldichlorosilane, no ethylsilane byproducts are detected.

Distillative working up of the crude product results in 2789 g (19.5 mols) of methylethyldichlorosilane, and hence in a yield of 98.5%, based on the vinyl chloride used.

We claim:

1. A process for the production of an ethylsilane, which comprises contacting vinyl chloride with hydrogen silane in the presence of a platinum or palladium catalyst at a pressure of not less than 5 bars.

2. A process according to claim 1, wherein the reaction is carried out at a pressure of between 8 and 25 bars.

3. A process according to either claim 1 or claim 2, wherein the catalyst is disposed on a carrier material which is disposed above the reaction mixture, which is kept boiling, between the reaction mixture and a condensing apparatus, the condensate of the reaction mixture being caused to trickle from the condensing apparatus over the catalyst.

4. A process according to claim 1, wherein the reaction mixture is kept boiling and the vapors rising therefrom are conducted to a condensing apparatus while the catalyst is bypassed and condensate is thereafter passed over said catalyst.

UNITED STATES PATENT AND TRADEMARK OFFICE
CERTIFICATE OF CORRECTION

PATENT NO. : 4,196,139
DATED : April 1, 1980
INVENTOR(S) : CLAUS-DIETRICH SEILER and HANS-JOACHIM VAHLENSIECK It is certified that error appears in the above-identified patent and that said Letters Patent are hereby corrected as shown below:

Column 1, line 21, "difficuit" should be --difficult--

Column 2, line 17, "υ" should be --γ--.

Column 3, line 14, "vinly" should be --vinyl--.

Signed and Sealed this

Twenty-ninth Day of July 1980

[SEAL]

Attest:

SIDNEY A. DIAMOND

Attesting Officer

Commissioner of Patents and Trademarks